(12) United States Patent
De Luca

(10) Patent No.: US 8,293,254 B2
(45) Date of Patent: Oct. 23, 2012

(54) SALTS OR COMPLEXES OF METHYL DONORS WITH PHYTIC ACID OR ITS DERIVATIVES AND METHOD FOR THE SYNTHESIS THEREOF

(76) Inventor: Maria De Luca, Bellona (IT)

( * ) Notice: Subject to any disclaimer, the term of this patent is extended or adjusted under 35 U.S.C. 154(b) by 738 days.

(21) Appl. No.: 11/923,000

(22) PCT Filed: Jun. 23, 2006

(86) PCT No.: PCT/IT2006/000484
§ 371 (c)(1),
(2), (4) Date: Feb. 17, 2009

(87) PCT Pub. No.: WO2007/004244
PCT Pub. Date: Jan. 11, 2007

(65) Prior Publication Data
US 2009/0175914 A1    Jul. 9, 2009

(30) Foreign Application Priority Data

Jun. 30, 2005 (IT) .............................. RM2005A0344

(51) Int. Cl.
*A61K 9/00* (2006.01)
*C07F 9/02* (2006.01)

(52) U.S. Cl. ........................... 424/400; 514/47; 558/156

(58) Field of Classification Search ................... 514/47; 424/400; 558/156
See application file for complete search history.

(56) References Cited

U.S. PATENT DOCUMENTS 7,799,782 B2 * 9/2010 Munson et al. ............ 514/234.5
2003/0078231 A1 * 4/2003 Wilburn ......................... 514/45

OTHER PUBLICATIONS

Holford, 2002 CAS: 137:375277.*

* cited by examiner

*Primary Examiner* — Rei-tsang Shiao
(74) *Attorney, Agent, or Firm* — Arent Fox LLP

(57) ABSTRACT

The invention concerns the production of salts or chelates of methyl donors, in particular S-adenosyl-L-methionine or SAMe and betaine or N,N,N-trimethylglycine, with phytic acid or with phosphorylate inositol, possibly partially salified with metal cations, with the formation of stable, totally natural, compounds having a biological activity typical of the starting methyl donors and also combined with, and enhanced by, the biological activity typical of phytic acid or of inositol. The invention also concerns nutraceutical, pharmaceutical, dietary, phytopharmaceutical or veterinary compositions comrising one or more salts or complexes of methyl donors with phytic acid or its derivatives and the method for the synthesis thereof.

17 Claims, 2 Drawing Sheets

Figure 1A:
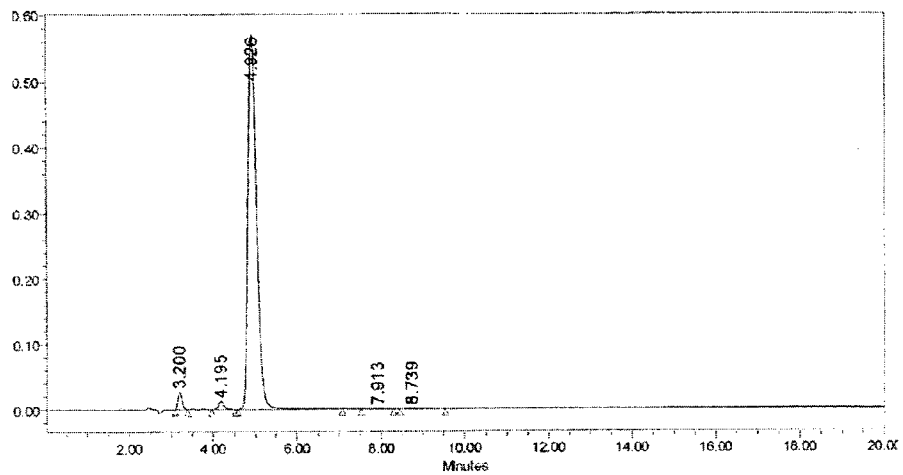

SALTS OR COMPLEXES OF METHYL DONORS WITH PHYTIC ACID OR ITS DERIVATIVES AND METHOD FOR THE SYNTHESIS THEREOF

The present invention concerns new salts or complexes of methyl donors with phytic acid or its derivatives and a method for the synthesis thereof. More specifically, the present invention concerns the production of salts or chelates of methyl donors, such as S-adenosyl-L-methionine or SAMe and betaine or trimethylglycine, with phytic acid or with phosphorylated inositol, with the formation of totally natural stable compounds having the typical biological activity of the starting methyl donors combined with, and enhanced by, the typical biological activity of phytic acid and of inositol.

As is well known, the term methyl donors is used to refer to the natural organic methylated substances that have biologically labile methyl groups which are easily passed to other molecules through a transmethylation reaction. Through this reaction methyl groups are supplied by a methyl donor molecule to another molecule, thus radically changing its chemical-physical properties and biological functions, thereby making possible the biosynthesis of molecules with well-defined physiological functions in the body's processes. The methylation reactions, which are catalysed by enzymes belonging to the transferase, transmethylase or methyltransferase class, influence, for instance, the gene expression, the function of cell membranes, and the action of various hormones and neurotransmitters. Actually, vitamins, hormones, neurotransmitters, nucleic acids, enzymes and antibodies all depend on methyl groups transfer for their synthesis and for carrying out their functions in the body.

In particular, methyl groups convert homocysteine [HS$(CH_2)_2CH(NH_2)$—COOH], which is a toxic amino acid, into the sulphur-containing amino acid methionine, [$CH_3S(CH_2)_2 CH(NH_2)COOH$], which is a beneficial amino acid, that is in turn a methyl donor present in all proteins. In fact, the body uses only small quantities of homocysteine and its accumulation can cause cardio-vascular disorders. To counter the foregoing, one detoxification mechanism the body possesses is actually methylation.

Among the natural substances having methyl donor activity—besides the already-mentioned amino acid methionine, and choline, another essential nutrient widely distributed in foods, which also has a molecule with easily transferable methyl groups, [$(CH_3)_3N^+(CH_2)_2OH$]—a pre-eminent one is SAM or SAMe, S-adenosyl-L-methionine (also known as ademethionine). It is a natural compound found in all living beings—bacteria, fungi, plants and animals, including man—and is the key element of many biochemical processes.

Products containing SAMe are composed of a mixture of two diastereoisomers: (RS)-(+)-SAMe and (SS)-(+)-SAMe, having the following structural formulas:

SS

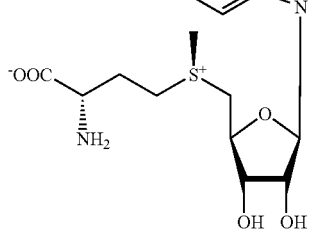

-continued

RS

It has been shown that only one of these two diastereoisomers, (SS)-(+)-SAMe, is biologically active for transmethylation, and that this racemises spontaneously, leading to the formation of the inactive diastereoisomer (RS)-(+)-SAMe. In living beings, SAMe is formed through the action of enzymes (S-adenosylmethionine synthetase or S-adenosyltransferase) in the cytoplasm, starting from the methionine taken in from food and from the ATP found as an energy reserve in any living cell.

SAMe carries out a fundamental function in many transmethylation processes linked to the body'vital biological functions, among which the conversion of the neurotransmitter serotonin into melatonin, the synthesis of creatine, that is a fundamental energy reserve of muscle tissue, the reintegration of glutathione, that is an important antioxidant, the biosynthesis of choline and phosphatidylcholine, of which choline is the precursor. Owing to its role in neurotransmitters synthesis, SAMe is used successfully in treating depression and also has applications in other medical fields, including chronic hepatic disorders, lipemia, adiposis and atherosclerosis.

Another methyl donor with important biological functions is betaine or trimethylglycine (TMG), more precisely N,N,N-trimethylglycine, having the formula [$(CH_3)_3N^+(CH_2) COO$]. The latter represents the oxidized analogue of choline, and is produced in the body in the frame of choline metabolism. This quaternary amino acid is widely found in plant and animals and is also present in large quantities in sugary molasses, in cotton seeds and in wheat germ. Its main form is anhydrous, 97% pure, appearing as a crystalline product. When ingested, it is rapidly converted through a transmethylation reaction, at the hepatic level, into the tertiary amino acid dimethylglycine (DMG), providing all the benefits typical of DMG for the improvement of cell metabolism, the immune system and oxygen use, and thus improving the body's adaptation to physical and mental strain.

Moreover, trimethylglycine is active like the other methyl donors in reducing the body's homocysteine levels, and is also recommended as a lipothropic agent and hepatoprotector in liver disorders.

In sum, therefore, the transfer of a methyl group of betaine results in a whole series of effects, due to the formation of dimethylglycine, that have led to finding useful applications of this methyl donor in the treatment of cardiovascular and hepatic pathologies, in sports medicine, in the treatment of diabetes, neurological alterations, hypoglycaemia, chronic fatigue, autism and more besides.

Returning now to the most commercial of the methyl donors, S-adenosyl-L-methionine, this molecule may either be obtained synthetically, via enzymatic synthesis from ATP and methionine, or through fermentation, starting from yeasts such as *Torulopsis utilis, Aspergillus tamarii, Saccharomyces cerevisiae*. The inactive component remains in the natural product in a percentage of around 20%, while the synthetic component presents 50% of biologically inactive product.

The main drawback of SAMe is its instability, both in solution and in crystalline form. Even at room temperature, the product racemises, degrades by splitting or undergoes hydrolysis, decomposing into 5'-methylthioadenosine and homoserine lactone. The chloride or sulphate salts are usable only as short-term reactives, but are not suitable for the production of commercial pharmaceutical products. In order to overcome this drawback, many saline forms of SAMe have been proposed over time, among which tri-p-toluenesulphonate (tri-tosylate)—which is disclosed by Italian patent No. 1043885, a double salt with sulphuric acid and p-toluenesulphonic acid (disulphate di-tosylate and disulphate tosylate)—which is disclosed by U.S. Pat. No. 3,954,726, salts with sulphonic acids or double salts, with sulphuric acid and sulphonic acids, which are disclosed by Italian patent No. 1054175. Moreover, because the aforesaid salts are not suitable for parenteral use, since their high acidity means that the concentration of buffer salt necessary for a pharmaceutically stable product would be excessive, salts of SAMe and 1,4-butanedisulphonate have also been proposed. Other SAMe salts suggested, still with a view to enabling the necessary stability to a product which, being marketable, must guarantee the absence of degradation for the storage period required by the specifications, are the salts obtained with the acyltaurines.

It must be noted that the SAMe salt-based products considered so far contain considerable amounts of xenobiotic substances: in tosylate disulphate, almost half the weight of the active ingredient is composed of synthetic xenobiotic substances, sulphuric acid and p-toluenesulphonic acid (384 mg of the product is equivalent to 200 mg of SAMe ion), and the same holds true for 1,4-butanedisulphonate (760 mg is equivalent to 400 mg of SAMe ion), in which the xenobiotic substance, butanedisulphonate, is mostly an organic compound of petrolchemical origin.

In both the aforesaid cases, the product may be dried through freeze-drying or spray-drying. The acidity of the product offers protection against the cleavage reaction, while the low amount water contents obtainable through freeze-drying or spray-drying protects the product against chemical hydrolysis. It has, however, been found that the in-vivo stability of SAMe is due to its bond with large anions, and high charge.

In the light of the above, it is evident that the production of a stable salt of SAMe according to the prior art teachings involves a high cost of the drying process and the need to use a xenobiotic counter-ion of completely non-natural origin, such as the ones mentioned above.

An object of the present invention is thus to provide a derivative of the SAMe methyl donor, or of other methyl donors such as the ones referred to above, wherein the salification—necessary in the case of SAMe to guarantee chemical stability to the product—is obtained without using any xenobiotic counter-ions, by means of an unexpensive process that is easy to carry out.

To this end, according to the present invention, there is proposed to salify the molecule representing the methyl donor, that is in particular—but not exclusively—SAMe, with a counter-ion chosen such that even the anionic part of the molecule, introduced through salification, is of natural origin and has in itself some biological functions useful for the therapeutic or nutraceutical activity of the resulting compound.

According to the present invention, it has been found that a completely natural substance, whose molecule is characterised by having a high density of negative charge, phytic acid, is able to salify SAMe and to determine, with a suitable solvent, its precipitation in water (in an ice bath), without needing to use complex procedures to separate the stable salt: from the precipitated and filtered salt, the residual water can be removed through a simple drying process at room temperature, by means of conventional drying agents such as calcium chloride or phosphoric anhydride.

Phytic acid or inositolhexaphosphoric acid [inositol hexakis(di-hydrogen phosphate)], is the hexaphosphoric ester of inositol, with a molecular weight of 660,04, empirical formula $C_6H_{18}O_{24}P_6$ and the following structural formula:

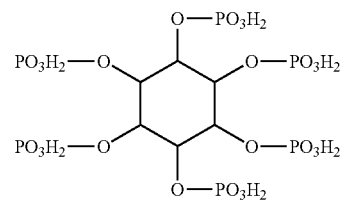

It is a compound widely found in nature, particularly in plants, where it is particularly abundant in oily seeds, cereals and pulses. It is also commercially available as it is or in solution in the form of sodium salt (sodium phytate) or as a mixed calcium and magnesium salt $[Ca_5Mg(C_6H_6O_{24}P_6)]$. In the latter form, it is called phytin and is used as a phosphorylated reconstituent and calcium supplement.

Phytic acid forms insoluble complexes with di- and trivalent cations and, owing to its chelant properties towards minerals, it has in the past been considered an anti-nutritional factor. It must be noted, however, that this natural antioxidant has shown a protective effect against carcinoma precisely because of its chelant properties (Shamsuddin, A. M., Elsayed, A. M. and Ullah, A.(1998), Suppression of large intestinal cancer in f344 rats by inositol hexaphosphate, *Carcinogenesis*, 9: 577-580). Moreover, ingested, phytic acid confers gastric satiety and slows down the digestion of amide by acting on post-prandial glycaemia levels. Digested by phytase, it yields inositol as a product, the corresponding hexahydroxylate product, which is also widely found in nature, where it is a growth factor for micro-organisms and higher-order animals.

It is thanks to its in-vivo transformation into inositol that phytic acid performs a series of biologically useful effects, for which its presence in a therapeutic or nutraceutical molecule is highly appreciable. Recent studies have highlighted not only its anti-tumour activity but also its antioxidant, hypocholesterolemizing and hypolipidemising activity.

As regards its anti-carcinogenic activity, epidemiological studies have shown that the use of soy products, which are an excellent natural source of phytic acid, leads to lower prostate cancer mortality rates. This is particularly due to the ability of phytic acid to chelate zinc, besides calcium, magnesium, copper and iron (Hebert, J. R., Hurley, T. G., Olendzki, B. C., Teas, J., Ma, Y. & Hampl, J. S: (1998), Nutritional and socio-economic factors in relation to prostate cancer mortality: a cross-national study, *J. Natl. Cancer Inst.*, 90:1637-1647; Kolonel, L. N., Hankin, J. H., Wittemore, A. S., Wu, A. H., Gallagher, R. P., Wilkens, L. R., et al. (2000) Vegetables, fruit, legumes and prostate cancer: a multiethnic case-control study, *Cancer Epidemial Biomarker Prev,* 9: 975-804).

In particular, inositol is active in cell membranes and in sending messages signalling the control of cell functions in the nervous system. Like choline, inositol is also present in lecithin and turns out to be effective for stimulating the production of lecithin itself in the body. Since fats are transferred from the liver to the cells with the help of lecithin, inositol positively contributes to the metabolism of fats and helps to reduce cholesterol levels in the blood. Moreover, the use of inositol along with choline has a positive effect on peripheral diabetic neuropathies, and the same combination is recommended also in women's nutrition and in cases of hypoglycaemia.

The daily intake of inositol with food is around 1 gram, from animal sources such as phospholipids, or from vegetable sources like phytic acid, while therapeutic doses range from 500 to 1,000 mg a day. Patients with peripheral neuropathies caused by diabetes were given 500 mg twice a day for two weeks, with considerable results. 3 g of myoinositol was also administered orally and 1 gram intravenously, without any appearance of side-effects or toxic effects.

Among the other useful biological effects of inositol, and thus of the phytic acid that constitutes its in-vivo precursor, it should be noted that inositol has an effect similar to that of sedatives, and does not only act as a tranquilliser without any side-effect, but may also be effective against insomnia. It clears up cases of slight hypertension by gradually lowering blood pressure, and is also useful in treating schizophrenia, hypoglycaemia and patients with high copper levels and low zinc levels in the blood. Finally, inositol has been found to prevent swelling of the liver.

Thus, the present invention specifically provides a salt or complex of a methyl donor compound with phytic acid or phosphorylated inositol, where by phosphorylated inositol it is meant a molecule in which one or more phosphoric groups of phytic acid are salified with metal cations, wherein the methyl donor compound may be selected from the group consisting of: S-adenosyl-L-methionine and N, N, N-trimethylglycine.

In the particular case where the methyl donor concerned is SAMe, the salts and complexes of SAMe and phytic acid or phosphorylated inositol, according to the present invention, have the following formula:

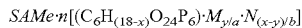

wherein:
SAMe is a molecule of S-adenosyl-L-methionine,
n is an integer ranging from 1 to 3,
x is a number comprised between 0 and 12 ($0 \leq x \leq 12$),
y is a number comprised between 0 and x ($0 \leq y \leq x$),
M and N are mono- or polyvalent metal cations,
a and b, respectively, are the oxidation state of M and N.

It is immediate to ascertain that the general formula above includes the particular cases in which SAMe is salified with phytic acid, with phytin (calcium and magnesium salt) or with any other simple or mixed salt of phytic acid with metal cations, such as sodium phytate or the calcium and iron salt of phytic acid.

In the other particular case where the methyl donor compound is betaine or N,N,N-trimethylglycine, the salts or complexes according to the present invention have the following formula:

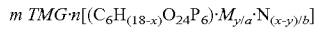

wherein:
TMG is a molecule of N,N,N-trimethylglycine,
m and n are integers ranging from 1 to 10,
x is a number ranging between 0 and 12 ($0 \leq x \leq 12$),
y is a number ranging between 0 and x ($0 \leq y \leq x$),
M and N are mono- or polyvalent metal cations,
a and b, respectively, are the state of oxidation of M and N.

In both the aforesaid preferred cases, the M and N cations, when present, are preferably cations of alkali metals or alkaline-earth metals and, in particular, they are calcium and magnesium.

According to a further aspect thereof, the present invention specifically provides a nutraceutical, pharmaceutical, dietary, phytopharmaceutical or veterinary composition comprising one or more salts or complexes of a methyl donor compound selected from the group consisting of S-adenosyl-L-methionine and N,N,N-trimethylglycine with phytic acid or with phosphorylated inositol, optionally partially salified with metal cations. Also in this case, specific embodiments of the present invention consist of the case wherein the methyl donor is SAMe, and the said salt or complex is represented by the aforesaid general formula, and the case wherein the methyl donor is betaine, and the salt or complex obtained according to the present invention is expressed by the corresponding general formula above. These two active ingredients can also be formulated in combination with one another.

The compositions proposed according to the present invention, besides presenting a storage stability that is beyond current expectations regarding SAMe, have the undoubted advantage of bringing together the biological activities of two different active ingredients within a single molecule, and of not containing xenobiotic components that are not biologically useful. In the case of SAMe, whose main desired activity is as an antidepressant, the additional presence—in the same molecule—of a metabolisable component like inositol, that per se has a stabilising effect on mood, can confer a synergic efficacy to the resulting preparation.

Moreover, as already noted, methyl donors in the form of complexes or salts with phytic acid have their antioxidant and preservation activities increased as regards certain kinds of cancer.

The preparations according to the present invention can be formulated on the basis of well-known techniques in the pharmaceutical field, and can be integrated, for example, with acidifying, drying, stabilising or antioxidant agents. They can be enriched with aromatising agents, sweeteners and other ingredients that are conventional in the specific application field and suitable to the administration form envisaged. The preparation can also be presented, in particular, in the microencapsulated form.

The present invention also specifically provides the use of one or more salts or complexes of a methyl donor compound with phytic acid or with phosphorylated inositol, optionally partially salified with metal cations, for the production of nutraceutical, pharmaceutical, dietary, phytopharmaceutical, cosmetic or veterinary preparations. As already noted, the methyl donor may be selected from the group consisting of S-adenosyl-L-methionine, N,N,N-trimethylglycine, N,N-dimethylglycine, choline and methionine, the most preferred products being the one in which the methyl donor is SAMe and the one in which the methyl donor is trimethylglycine.

In particular, the preparations containing the salts according to the present invention can be used as products with antidepressant activity or in any case acting on the central nervous system, products for treating obesity, phosphorous dietary supplements, calcium dietary supplements and magnesium dietary supplements, hepatoprotector preparations, products with dermatological activity and products with anti-tumour activity, not only in man, but also in all other hot-blooded vertebrates.

Finally, according to a further aspect thereof, the present invention concerns an extremely simple and unexpensive synthesis process by which salts or complexes of the proposed methyl donors can be obtained. In general, the process comrprises the following fundamental operations:

a) solubilising the methyl donor compound or a salt thereof in a suitable solvent;
b) adding a pre-established quantity of phytic acid or phosphorylated inositol;
c) adding to the reaction mixture a solvent in which the desired salt or complex is insoluble;
d) collecting and filtering the resulting precipitate;
e) drying or allowing the said precipitate to dry.

For the production of salts or complexes of phytic acid with trimethylglycine, the said operation a) is carried out by solubilising N,N,N-trimethyl glycine base in distilled water and, after operation b), calcium chloride or magnesium chloride is added to the reaction mixture; further, in the said operation c), ethanol or another suitable solvent is added, and the whole mixture is left at 4° C. until complete precipitation is obtained. Finally, after filtration d), the said operation e) is carried out at room temperature in the presence of a drying agent.

The production, according to the aforesaid procedure, of salts or complexes of SAMe can be carried out with alternative procedures, depending on whether SAMe is made to react in a form already salified with one of the anions of the prior art, directly with phytic acid or with phosphorylated inositol (phytin) and, in the latter case, depending on whether the anion eliminated from SAMe is preventively extracted or not before phytin is added. According to a specific embodiment of the aforesaid general procedure, operation a) is carried out by solubilising a salt of SAMe in distilled water and operation b) is performed with phytic acid; after the said operation b), the reaction mixture is left under stirring in an ice bath; in operation c), ethanol or another suitable solvent is added and the whole mixture is left in an ice bath until complete precipitation is obtained. Finally, after filtration d), operation e) is carried out in the presence of a drying agent.

According to a different specific embodiment, operation a) is carried out by solubilising a salt of SAMe in distilled water, and after this operation, the anion originally present in the SAMe salt—in particular, the sulphate—is made to precipitate as a salt by adding a suitable agent, and particularly barium chloride; then, operation b) is carried out by adding phytin, and then some drops of concentrated sulphuric acid are added and the reaction mixture is left under stirring in an ice bath. In operation c), ethanol is added and the whole mixture is left in an ice bath until complete precipitation is obtained. Finally, after filtration d), operation e) is carried out in the presence of a drying agent.

According to some specific solutions, the said drying agent is calcium chloride or phosphoric anhydride.

Although one of the most advantageous features of the process according to the present invention is that of doing without the demanding freeze-drying and spray-drying processes to obtain the desired product in crystalline and dry form, it is possible to substitute the said operation e) with a spray-drying or a freeze-drying operation, to be implemented directly on the solution of salt or complex obtained according to the first steps of the process of the present invention.

Figure 1B:
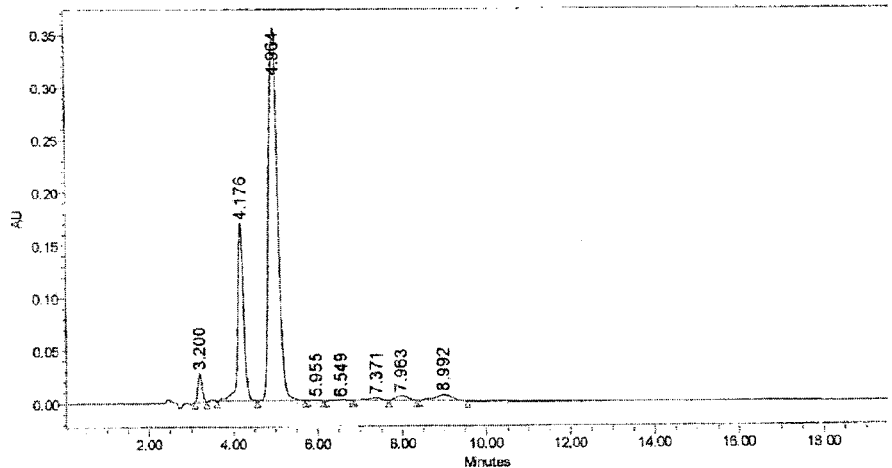
Figure 2A:
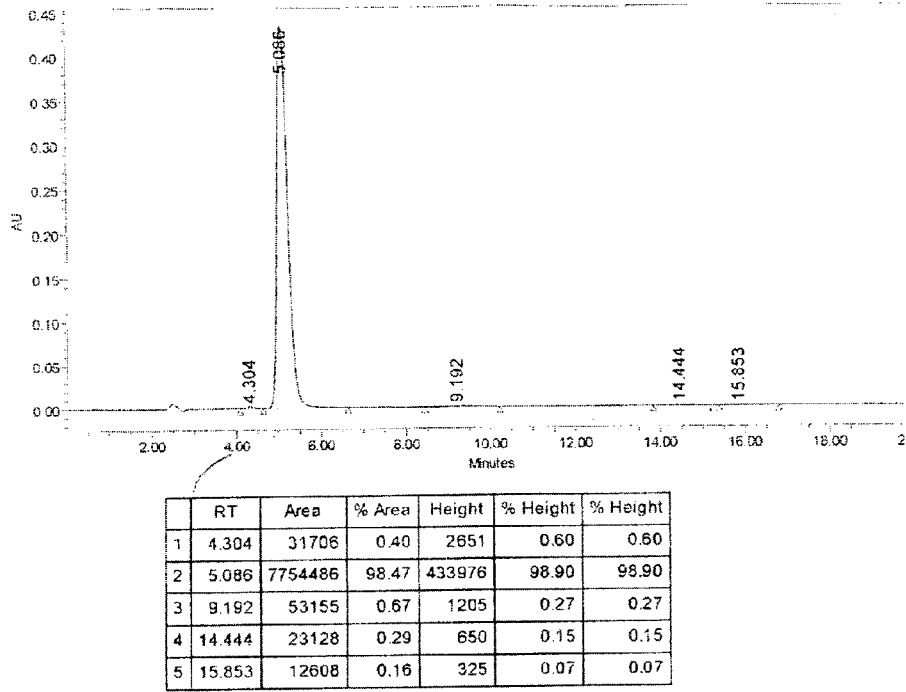
Figure 2B:
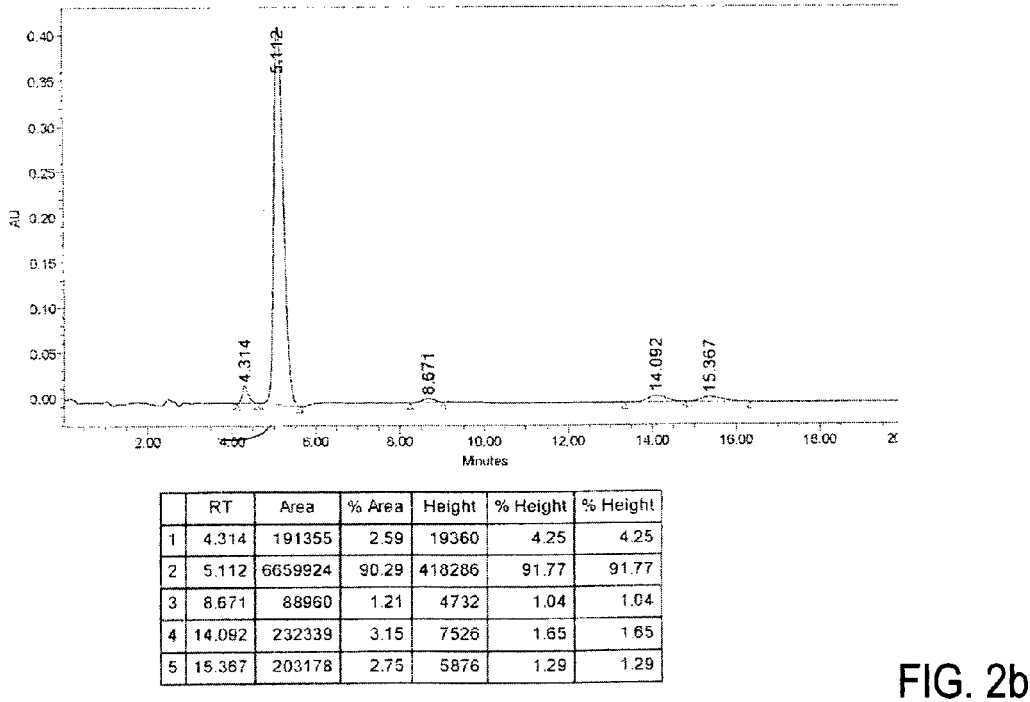

The specific features of the present invention, as well as its advantages and relative operating procedures, will be more evident with reference to the detailed description presented merely by way of example below, together with the results of the experimentation carried out on the invention. Some experimental results are also illustrated in the attached drawings, wherein:

FIGS. 1a and 1b show the chromatogram of a physical mixture of 50% phytin and 50% SAMe disulphate tosylate, respectively immediately after preparation and after a period of 5 days at 53° C.; and FIGS. 2a and 2b show the chromatogram of a SAMe phytate complex according to the present invention, respectively after preparation and after a period of 5 days at 53° C.

Some specific embodiments of the synthesis according to the present invention are reported in the following examples.

EXAMPLE 1

Synthesis of SAMe Phytate Salt

In the following example, SAMe in ionic form was obtained directly from fermented yeast. The preparation according to the present invention was carried out according to the following procedure.

SAMe ion 1 mole;
phytin 1 mole;
add ⅔ drops of concentrated sulphuric acid;
cold mix the three products in an ice bath;
add ethanol until complete precipitation of the SAMe phytate is obtained;
filter the precipitate with a paper filter and leave to dry in a drier with calcium chloride or phosphoric anhydride.
Recovery>90%.

After complete drying, the crystalline salt-looking product has the appearance of a soft white powder. Chemical analysis reveals the actual salification of about one mole of phytic acid with one mole of SAMe ion.

The product turned out to be very stable during 5 days at 53° C.

The above reaction can also be obtained by using phytic acid instead of phytin; calcium and/or magnesium is added to obtain the precipitate.

Finally, it must be noted that the chelation of SAMe with phytate is useful also to roughly separate the SAMe from the culture broths.

COMPARATIVE EXAMPLE

Physical mixture of SAMe disulphate tosylate and phytin

In order to evaluate the stability of a simple, non-salified or complexed, mixture of the same ingredients as in the previous example, phytin and SAMe disulphate tosylate were simply dry mixed in equal proportions (50% phytin, 50% SAMe disulphate tosylate).

The evaluation of the degradation was carried out by HPCEC-UV analysis using 0.5M (pH 4) ammonium formiate as an eluent, a flow of 1.2 ml/min, and a Supelcosil LC-SCX column (25 cm, 4.6 mm, 5 micron).

The chromatograms obtained from the mixture, immediately after its preparation and after 5 days at 53° C., are shown respectively in FIGS. 1a and 1b, which are also accompanied by numerical tables with the values found. As it can be seen, after 5 days at 53° C. there is a loss of active ingredient higher than 24%.

EXAMPLE 2

Synthesis of SAMe Phytate Salt

Starting from a commercially available SAMe salt, SAMe disulphate tosylate, the synthesis of the product according to the present invention was carried out according to the following procedure.

1. solubilise 400 mg of SAMe disulphate tosylate in 2.5 ml of distilled water;
2. extract in ether (5 ml) the p-toluenesulphonic acid (PTSA) by using a separating funnel;
3. precipitate the sulphates contained in the aqueous phase (after extracting the PTSA) with 0.254 mg of barium chloride, and centrifuge for 5 minutes at 4000 rpm (T=4° C.);
4. to the supernatant, slowly add (under magnetic stirring) 410 mg of phytin suspended in 2.5 ml of water;
5. add ⅔ drops of sulphuric acid;
6. leave in an ice bath for 10 minutes (the pH of the solution corresponds to 1.3);
7. add 20 ml of 95% ethanol and leave in an ice bath until complete precipitation is obtained; a very white precipitate forms;
8. separate the precipitate by filtering on paper (vacuum beaker with pump);
9. let the precipitate dry at room temperature in the presence of calcium chloride or phosphoric anhydride; after 24 hours the product turns into a white crystalline powder.

It was also found that the aforesaid step 2 of the process can be avoided.

Starting from a SAMe ion solution, the SAMe ion and the sulphates are titrated: the ratio between moles of sulphates and moles of barium is 1:1. The same is also true for the molar ratio between SAMe ion and phytic acid of phytin, for the next step.

The reaction yields about 600-700 mg of SAMe phytate. From 0 to 10% of the starting SAMe is left in the mother liquor.

The mean analysis on 3 laboratory lots for the aforesaid synthesis is summarised in the following table.
(Table 1 follows)

TABLE 1

|  | Lot 1 % p/p | Lot 2 % p/p | Lot 3 % p/p | Mean % p/p |
|---|---|---|---|---|
| SAMe ion | 25.0 | 25.3 | 25.4 | 25.2 |
| Phytic acid | 55.5 | 56.7 | 54.9 | 55.7 |
| Calcium | 5.5 | 5.2 | 5.1 | 5.2 |
| Mg | 1.48 | 1.35 | 1.52 | 1.45 |
| Sulphates | 2.1 | 2.3 | 2.5 | 2.3 |
| Humidity | 1.9 | 1.8 | 1.5 | 1.7 |
|  | 91.48 | 92.65 | 90.92 | 91.55 |

EXAMPLE 3

Synthesis of Same Salt with Phytic Acid and Evaluation of Stability

Starting from another commercially available SAMe salt, SAMe 1,4-butanedisulphonate, the synthesis of the product according to the present invention was carried out according to the following procedure.
1. solubilise 760 mg of SAMe 1,4 butanedisulphonate in 2 cc of water;
2. to the solution of step one, directly add 4.95 g of a 40% solution of phytic acid;
3. leave under stirring for an hour in an ice bath;
4. add 95% ethanol until complete precipitation is obtained (in an ice bath);
5. filter under vacuum;
6. dry for 2448 hours in a drier with calcium chloride or phosphoric anhydride.

The product thus obtained was subjected to stability trials according to a procedure similar to the one adopted for the Comparative Example above. The SAMe phytate complex according to the present invention and, simultaneously, a physical mixture obtained by dry mixing phytin and SAMe disulphate tosylate, in equal proportions (50% phytin, 50% SAMe disulphate tosylate), were subjected to stability trials which yielded the results shown in the table below.

Also in this case, the evaluation of the degradation was carried out by HPCEC-UV analysis using 0.5M ammonium formiate (pH 4) as an eluent, a flow of 1.2 ml/min, and a Supelcosil LC-SCX column (25 cm, 4.6 mm, 5 µm).

TABLE 2

|  | Lot 1 % p/p | Lot 2 % p/p | Lot 3 % p/p | Mean % p/p |
|---|---|---|---|---|
| SAMe ion | 25.2 | 25.1 | 25.3 | 25.2 |
|  | After 5 days at 53° C. | | | |
| SAMe ion | 23.2 | 23.3 | 23.2 | 23.2 |
|  | −7.9 | −7.2 | −8.3 | −7.8 |

TABLE 3

|  | Lotto 1 % p/p | Lotto 2 % p/p | Lotto 3 % p/p | Media % p/p |
|---|---|---|---|---|
| SAMe ion | 25.0 | 25.2 | 25.1 | 25.1 |
|  | After 5 days at 53° C. | | | |
| SAMe ion % Variation | 18.8 −24.8 | 19.7 −21.8 | 19.1 −23.9 | 19.2 −23.5 |

The difference of the mean % variations of the two groups, carried out by means of the student t test, was highly significant p<0.01.

The chromatograms obtained from the SAMe phytate complex according to the procedure of the present example, both immediately after preparation and after 5 days at 53° C., are shown in FIGS. 2a and 2b, respectively, which are also accompanied by numerical tables with the values found.

EXAMPLE 4

Synthesis of Betaine Salt with Phytic Acid

Starting from N,N,N-trimethylglyicine base (betaine), the complex with phytic acid according to the present invention was obtained through the following procedure.
1. solubilise 1.19 g of betaine base in 2.5 ml of distilled water;
2. add 1.65 g of a solution of 40% phytic acid;
3. leave the solution at room temperature and add 0.550 g of calcium chloride;
4. add 25 ml of 95% ethanol to the solution and leave the whole mixture at 4° C. until complete precipitation is obtained;
5. separate the white precipitate by filtering on paper (vacuum beaker);
6. leave the precipitate to dry at room temperature in the presence of a suitable drying agent; after 24 hours the product looks like a crystalline white powder.

Alternatively, in step 3, 0.470 g of magnesium chloride can be added instead of calcium chloride.

The present invention has been disclosed with particular reference to some specific embodiments thereof, but it should be understood that modifications and changes may be made by the persons skilled in the art without departing from the scope of the invention as defined in the appended claims.

I claim:

1. A salt or complex of a methyl donor compound selected from the group consisting of S-adenosyl-L-methionine and N,N,N-trimethylglycine with phytic acid or with phosphorylated inositol, wherein the phosphorylated inositol is phytic acid having one or more phosphoric groups salified with metal cations, and wherein the salt or complex of a methyl donor compound has the following formula:

$$SAMe \cdot n[(C_6H_{(18-x)}O_{24}P_6) \cdot M_{y/a} \cdot N_{(x-y)/b}]$$

wherein:
SAMe is a molecule of S-adenosyl-L-methionine,
n is an integer ranging from 1 to 3,
$0 \leq x \leq 12$
$0 \leq y \leq x$,
M and N are mono- or polyvalent metal cations,
a and b are, respectively, the state of oxidation of M and N; or the following formula:

$$m\,TMG \cdot n[(C_6H_{(18-x)}O_{24}P_6) \cdot M_{y/a} \cdot N_{(x-y)/b}]$$

wherein:
TMG is a molecule of N,N,N-trimethylglycine,
m and n are integers ranging between 1 and 10,
$0 \leq x \leq 12$,
$0 \leq y \leq x$,
M and N are mono- or polyvalent metal cations,
a and b are, respectively, the state of oxidation of M and N.

2. A salt according to claim 1, wherein said methyl donor compound is S-adenosyl-L-methionine, having the following formula:

$$SAMe \cdot n[(C_6H_{(18-x)}O_{24}P_6) \cdot M_{y/a} \cdot N_{(x-y)/b}]$$

wherein:
SAMe is a molecule of S-adenosyl-L-methionine,
n is an integer ranging from 1 to 3,
$0 \leq x \leq 12$,
$0 \leq y \leq x$,
M and N are mono- or polyvalent metal cations,
a and b are, respectively, the state of oxidation of M and N.

3. A salt according to claim 1, wherein said methyl donor is N,N,N-trimethylglycine, having the following formula:

$$m\,TMG \cdot n[(C_6H_{(18-x)}O_{24}P_6) \cdot M_{y/a} \cdot N_{(x-y)/b}]$$

wherein:
TMG is a molecule of N,N,N-trimethylglycine,
m and n are integers ranging between 1 and 10,
$0 \leq x \leq 12$,
$0 \leq y \leq x$,
M and N are mono- or polyvalent metal cations,
a and b are, respectively, the state of oxidation of M and N.

4. A salt according to claim 2, wherein said cations M and N are alkali metal cations or alkaline-earth metal cations.

5. A salt according to claim 4, wherein said cations are calcium and magnesium.

6. A nutraceutical, pharmaceutical, dietary, phytopharmaceutical or veterinary composition comprising one or more salts or complexes of a methyl donor compound selected from the group consisting of S-adenosyl-L-methionine and N,N,N-trimethylglycine with phytic acid or with phosphorylate inositol, wherein the phosphorylated inositol is phytic acid having one or more phosphoric groups salified with metal cations, and wherein the salts or complexes of a methyl donor compound have the following formula:

$$SAMe \cdot n[(C_6H_{(18-x)}O_{24}P_6) \cdot M_{y/a} \cdot N_{(x-y)/b}]$$

wherein:
SAMe is a molecule of S-adenosyl-L-methionine,
n is an integer ranging from 1 to 3,
$0 \leq x \leq 12$,
$0 \leq y \leq x$,
M and N are mono- or polyvalent metal cations,
a and b are, respectively, the state of oxidation of M and N; or the following formula:

$$m\,TMG \cdot n[(C_6H_{(18-x)}O_{24}P_6) \cdot M_{y/a} \cdot N_{(x-y)/b}]$$

wherein:
TMG is a molecule of N,N,N-trimethylglycine,
m and n are integers ranging between 1 and 10,
$0 \leq x \leq 12$,
$0 \leq y \leq x$,
M and N are mono- or polyvalent metal cations,
a and b are, respectively, the state of oxidation of M and N.

7. A composition according to claim 6, wherein said methyl donor compound is S-adenosyl-L-methionine and said salt or complex is as defined in claim 2.

8. A composition according to claim 6, wherein said methyl donor compound is N,N,N-trimethylglycine and said salt or complex is as defined in claim 3.

9. A composition according to claim 6, comprising a combination of a salt or complex of S-adenosyl-L-methionine and a salt or complex of N,N, N-trimethylglycine.

10. A composition according to claim 6 in a microencapsulated form.

11. A process for the production of salts or complexes of methyl donor compounds selected from the group consisting of S-adenosyl-L-methionine and N,N,N-trimethylglycine with phytic acid or with phosphorylated inositol, wherein the phosphorylated inositol is phytic acid having one or more phosphoric groups salified with metal cations, including the following operations:
a) solubilising the methyl donor compound or a salt thereof in a suitable solvent;
b) adding a pre-established quantity of phytic acid or phosphorylated inositol;
c) adding to the reaction mixture a solvent in which the desired salt or complex is insoluble;
d) collecting and filtering the resulting precipitate;
drying or allowing the said precipitate to dry, and
wherein the salts or complexes of methyl donor compounds have the following formula:

$$SAMe \cdot n[(C_6H_{(18-x)}O_{24}P_6) \cdot M_{y/a} \cdot N_{(x-y)/b}]$$

wherein:
SAMe is a molecule of S-adenosyl-L-methionine,
n is an integer ranging from 1 to 3,
$0 \leq x \leq 12$,
$0 \leq y \leq x$,
M and N are mono- or polyvalent metal cations,
a and b are, respectively, the state of oxidation of M and N; or the following formula:

$$m\,TMG \cdot n[(C_6H_{(18-x)}O_{24}P_6) \cdot M_{y/a} \cdot N_{(x-y)/b}]$$

wherein:
TMG is a molecule of N,N,N-trimethylglycine,
m and n are integers ranging between 1 and 10,
$0 \leq x \leq 12$,
$0 \leq y \leq x$,
M and N are mono- or polyvalent metal cations,
a and b are, respectively, the state of oxidation of M and N.

12. A process according to claim 11, wherein said methyl donor compound is N,N,N-trimethylglycine and said operation a) is carried out by solubilising N,N,N-trimethylglycine base in distilled water; after said operation b), calcium chloride or magnesium chloride is added to the reaction mixture; in said operation c), ethanol is added as the solvent and the whole mixture is left at 4° C. until complete precipitation is obtained; finally, said operation e) is carried out at room temperature in the presence of a drying agent.

13. A process according to claim 11, wherein said methyl donor compound is S-adenosyl-L-methionine (SAMe) and said operation a) is carried out by solubilising a salt of SAMe in distilled water; said operation b) is carried out with phytic acid; after said operation b), the reaction mixture is left under stirring in an ice bath; in said operation c), ethanol is added as the solvent and the whole mixture is left in an ice bath until complete precipitation is obtained; finally, said operation e) is carried out in the presence of a drying agent.

14. A process according to claim 11, wherein said methyl donor compound is S-adenosyl-L-methionine (SAMe) and said operation a) is carried out by solubilising a salt of SAMe in distilled water; after said operation a), the anion originally present in the SAMe salt is made to precipitate as a salt by adding a suitable agent; said operation b) is carried out by adding phytin; after said operation b), concentrated sulphuric acid is added and the reaction mixture is left under stirring in an ice bath, in said operation c), ethanol is added and the whole mixture is left in an ice bath until complete precipitation is obtained; finally, said operation e) is carried out in the presence of a drying agent.

15. A process according to claim 11, wherein said drying agent is calcium chloride or phosphoric anhydride.

16. A process according to claim 11, wherein, as an alternative to said drying operation e), said precipitate is dried by spray-drying or by freeze-drying.

17. A method of treating a condition, comprising administering the composition according to claim 6, wherein the condition is selected from the group consisting of depression, obesity, lipemia, adiposis, atherosclerosis, diabetes, hypoglycaemia, chronic fatigue, autism, prostate cancer, peripheral neuropathies, insomnia, hypertension, schizophrenia, and liver swelling.

* * * * *